US009561133B2

(12) United States Patent
Torello et al.

(10) Patent No.: US 9,561,133 B2
(45) Date of Patent: Feb. 7, 2017

(54) DRAIN VALVE IMPLANTABLE IN THE EYE OF A PATIENT FOR THE TREATMENT OF GLAUCOMA

(71) Applicant: ITH T3 PLUS S.R.L., Pontedera (IT)

(72) Inventors: Giulio Torello, Pisa (IT); Alfredo Ricci, Pontedera (IT)

(73) Assignee: ITH T3 PLUS S.R.L., Pontedera (IT)

( * ) Notice: Subject to any disclaimer, the term of this patent is extended or adjusted under 35 U.S.C. 154(b) by 0 days.

(21) Appl. No.: 14/890,487

(22) PCT Filed: May 12, 2014

(86) PCT No.: PCT/IB2014/061378
§ 371 (c)(1),
(2) Date: Apr. 14, 2016

(87) PCT Pub. No.: WO2014/184725
PCT Pub. Date: Nov. 20, 2014

(65) Prior Publication Data
US 2016/0242962 A1    Aug. 25, 2016

(30) Foreign Application Priority Data

May 13, 2013  (IT) .............................. MI2013A0783

(51) Int. Cl.
*A61M 5/00* (2006.01)
*A61F 9/007* (2006.01)
(52) U.S. Cl.
CPC ................................. *A61F 9/00781* (2013.01)
(58) Field of Classification Search
CPC ................................................. A61F 9/00781
(Continued)

(56) References Cited

U.S. PATENT DOCUMENTS 5,411,473 A    5/1995  Ahmed
5,433,701 A    7/1995  Rubinstein
(Continued)

OTHER PUBLICATIONS

International Preliminary Report on Patentability of PCT/IB2014/061378 of Aug. 21, 2015.
(Continued)

*Primary Examiner* — Philip R Wiest
(74) *Attorney, Agent, or Firm* — Silvia Salvadori, PC.; Silvia Salvadori

(57) ABSTRACT

A drain valve (10) implantable surgically in the eye (O) of a patient for the treatment of glaucoma, comprising a main body (11), and a drainage tube (12), connected at one end with the main body (11) and provided to be implanted in the eye (O) so as to penetrate with its distal tip inside the anterior chamber (CA) of the eye globe (GO), so as to allow the drainage outwards of the aqueous humour (UA), wherein the valve (10) is characterized by a series of significant improvements, including:
1) an extractable configuration (12a, 12b) of the drainage tube (12), to allow the adaptation (f1) of the length of the drainage tube (12) during the surgical operation to implant the valve (10);
2) a flattened or flat shape in section (12') of the drainage tube (12, 12a, 12b) suitable for reducing the dimensions in the radial direction (IR) of the drainage tube (12) with respect to the surface of the eye globe (GO);
3) a connection free from encumbrances between the tip portion (12f) of the drainage tube (12), provided to penetrate inside the eye globe (GO, CA), and the remaining part (12b') of the drainage tube (12);
4) a series of retaining bags or compartments (11b), formed along the lower or soffit surface (S") of the main body (11) in contact with the surface of the eye globe (GO), wherein these retaining bags (11b) are associated with respective through holes (11a) extended through the same main body (11) of the valve and are suitable
(Continued)

for receiving and retaining the aqueous humour (UA), so as to improve lubrication of the eyeball in the zone of the valve, once implanted;

5) a divergent fan-shaped opening (11c) formed on the extrados (S'), not in contact with the eye globe, of the main body (11) of the valve, in order to convey the aqueous humour (UA) and improve the lubrication around the drain valve (10), once implanted; and 6. a modified configuration, with respect to conventional drain valves, such as to allow, during the surgical operation, an arrangement, closer to the iris, of the holes (11d) for the insertion of the yarn for fixing the valve to the surface of the eye globe.

Thanks to these improvements the drain valve (10) ensures considerably improved and superior performances with respect to the currently known drain valves in use in the medical field for treating glaucoma.

9 Claims, 7 Drawing Sheets

(58) Field of Classification Search
USPC .................................................. 604/8–10
See application file for complete search history.

(56) References Cited

U.S. PATENT DOCUMENTS

| | | |
|---|---|---|
| 5,476,445 A | 12/1995 | Baerveldt et al. |
| 5,743,869 A | 4/1998 | Ahmed |
| 2005/0267398 A1 | 12/2005 | Protopsaltis et al. |
| 2010/0249691 A1 | 9/2010 | Van Der Mooren et al. |

OTHER PUBLICATIONS

International Search Report and Written Opinion of PCT/IB2014/061378 of Oct. 21, 2014.

Invitation to pay additional fees and, where applicable, protest fee for PCT/IB2014/061378 of Aug. 29, 2014.

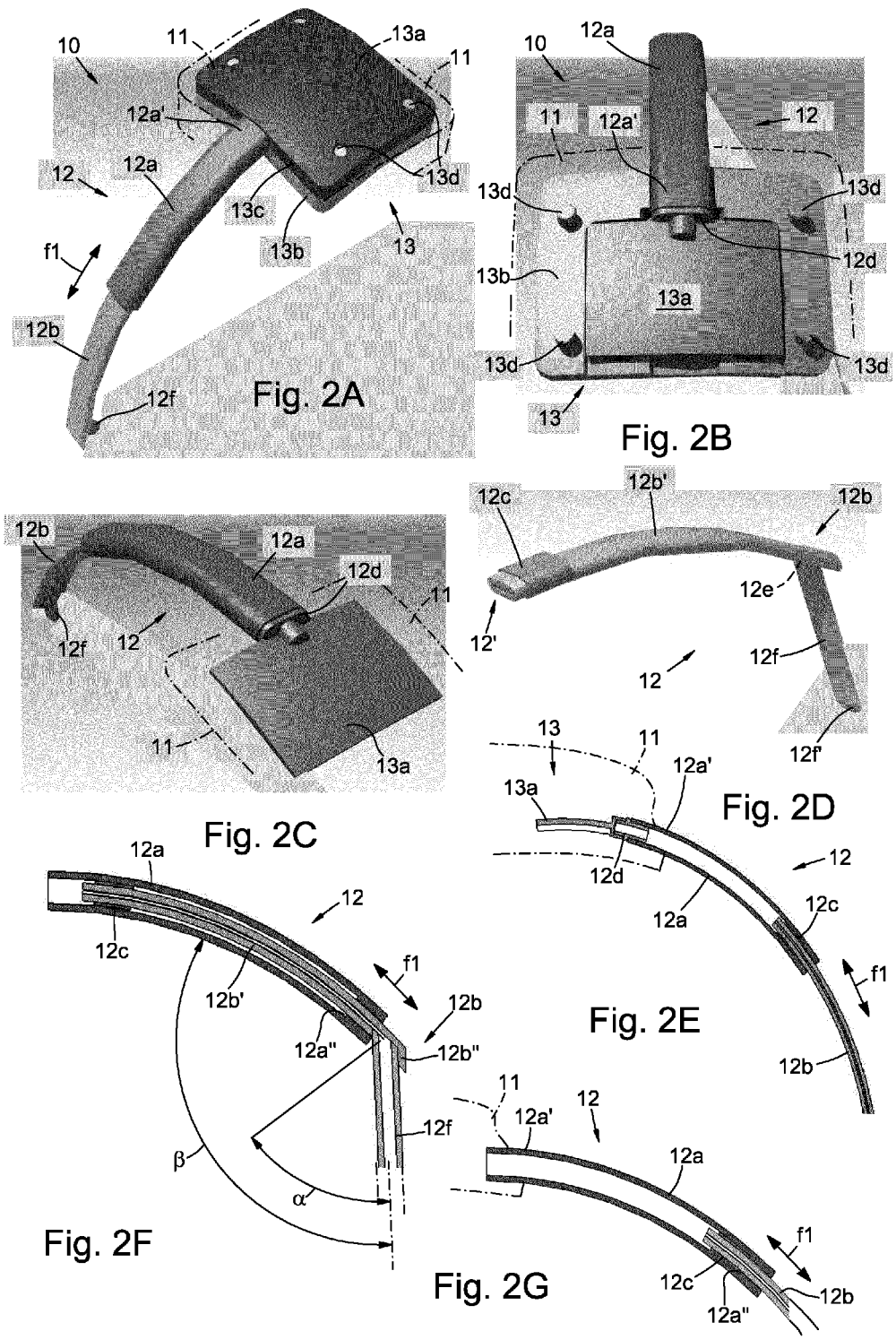

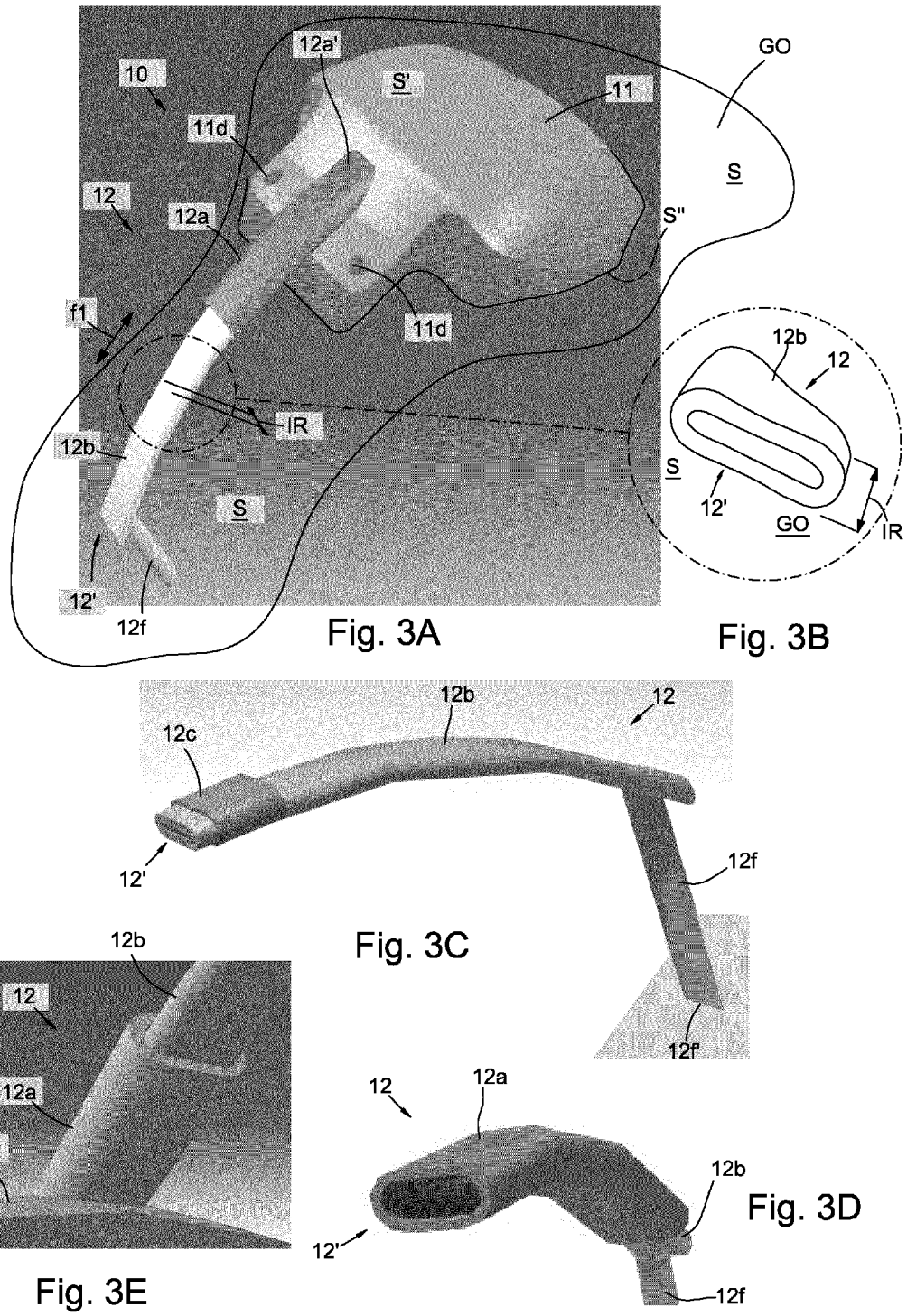

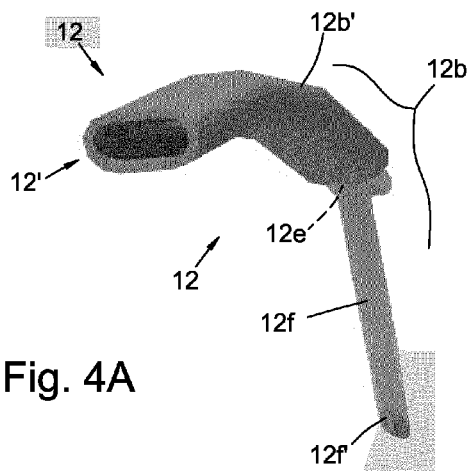
Fig. 4A
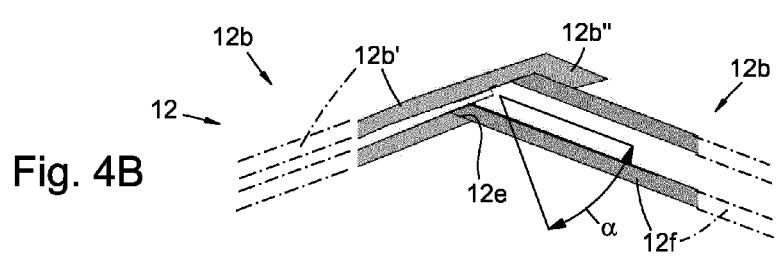
Fig. 4B
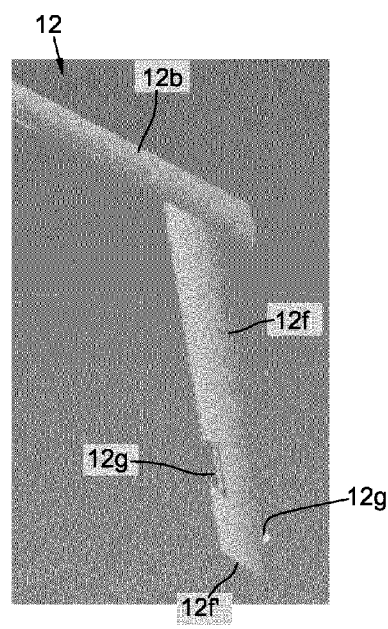
Fig. 4D
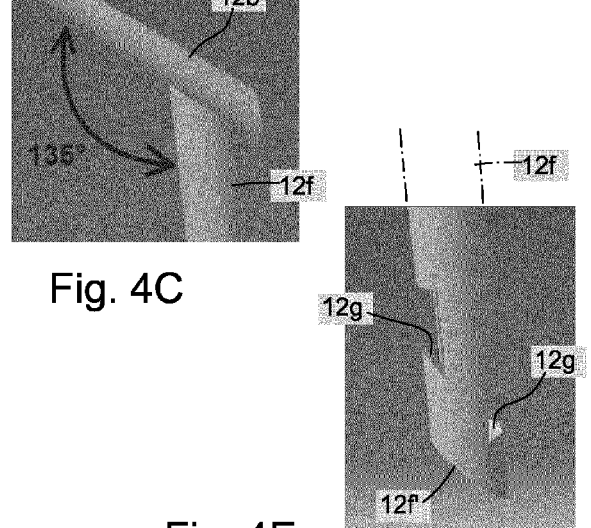
Fig. 4C
Fig. 4E

TECNICA NOTA

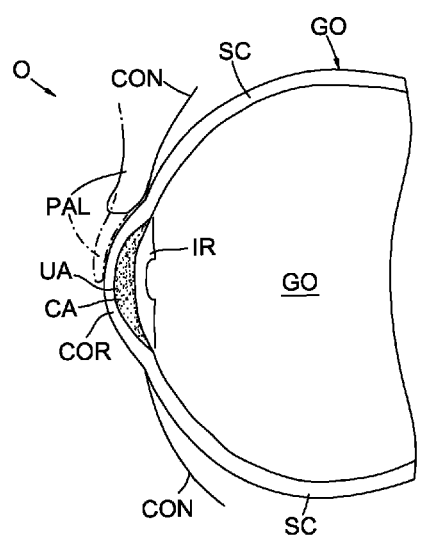
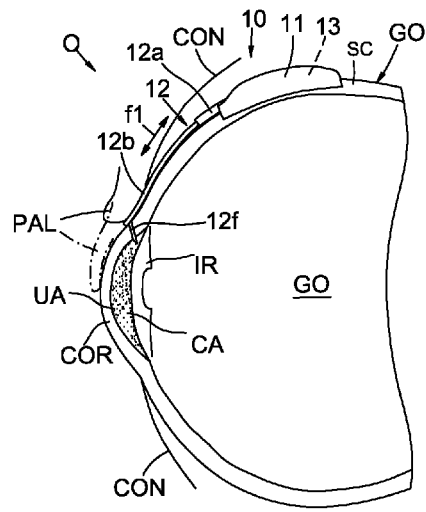
Fig. 9A     Fig. 9B
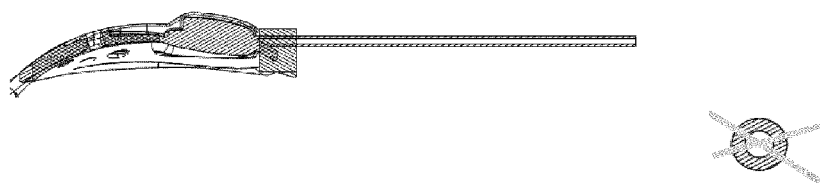
Fig. 8
TECNICA NOTA

DRAIN VALVE IMPLANTABLE IN THE EYE OF A PATIENT FOR THE TREATMENT OF GLAUCOMA

This application is a U.S. national stage of PCT/IB2014/061378 filed on 12 May 2014, which claims priority to and the benefit of Italian Application No. MI2013A000783 filed on 13 May 2013, the contents of which are incorporated herein by reference in their entireties.

DESCRIPTION

Field of the Invention

The present invention relates in general to the sector of implantable medical devices for the treatment and therapy of eye disease, and more particularly it relates to a drain valve suitable for being surgically implanted in the eye of a patient suffering from glaucoma in order to drain outwards the aqueous humour contained in the anterior chamber, between cornea and iris, of the eye, and therefore reduce the pressure of the aqueous humour inside the eye globe.

BACKGROUND OF THE INVENTION AND PRIOR ART

The prior art in the field of the invention offers implantable drain valves for the treatment of glaucoma which typically comprise a main body which in turn is associated with a drainage tube, connected at one end to the main body.

The main body of the drain valve is implanted by the surgeon on the surface of the eye globe of the patient, in an area under the conjunctiva, while the drainage tube is implanted so as to penetrate with its tip inside the anterior chamber and therefore drain the aqueous humour therefrom.

More particularly the drainage tube has a first end which is connected to the main body of the drain valve and a second distal end, opposite the one connected to the main body, which is implanted by the surgeon, during the operation, so as to perforate with its tip the surface of the eye globe and therefore penetrate inside the respective anterior chamber.

In this way the drain valve, once implanted by the surgeon in the eye of the patient, allows, by means of the distal end of the drainage tube which penetrates the anterior chamber, the drainage of the aqueous humour from the inside to the outside of the eye globe where the aqueous humour is received by the main body of the valve, to then flow to the exterior of the same main body in an area below the conjunctiva.

The implant of this valve, with consequent drainage of the aqueous humour contained in the eye globe, is such as to reduce considerably the intraocular pressure so as to be effective in the treatment of glaucoma from which the patient is suffering.

In known drain valves the respective drainage tube, which is implanted in the eye of the patient so as to penetrate the interior of the eye globe, and in particular the portion, of the drainage tube, which is connected and adjacent to the main body of the valve and is therefore placed, in the surgical operation, over the external surface of the eye globe, usually has a circular section.

Now this particular circular shape in section of the drainage tube is such as to generate an encumbrance, on the ocular surface, which in turn is found to be the cause of discomfort for the patient in whom the valve has been implanted, given that this encumbrance hinders the movement of the eyelids which have to close and open often to lubricate the ocular surface.

For completeness of information, FIG. 8 of the drawings shows a drain valve, of the conventional type and complying with the prior art, which has a drainage tube exhibiting such a circular section.

These however are not the only disadvantages, limits and defects of the drain valves known and currently used in the medical field for the treatment of glaucoma.

In fact the drain valves currently available for the treatment of glaucoma do not appear such as to respond satisfactorily to some major needs and necessities which could arise and which the surgeon could have during the operation for implanting the drain valve.

For example known drain valves do not allow the surgeon to adapt, i.e. increase or decrease, the distance between the point wherein the drainage tube is implanted, and therefore penetrates the interior of the eye, and the valve itself, according to the specific circumstances and situations of the surgical operation to implant the valve in the eye of the patient.

Moreover a last but not least disadvantage, which can be found in known drain valves, is due to poor lubrication, in turn the potential cause of infections, which occurs in the zone of contact between the body of the drain valve and the outer surface of the eye globe whereon this body is implanted.

More particularly this considerable disadvantage occurs despite the fact that the main body of known drain valves is at times provided with several through holes which allow the placing in communication of the zone of the outer surface of the eye globe, on which the valve is placed and implanted, with the upper surface of the main body of the valve where the drained aqueous humour coming from inside the eye globe flows.

A further limit and disadvantage of known drain valves is connected to the fact that, in order to secure stably during the surgical operation the main body of the drain valve on the eye globe, the fixing holes, for the insertion of the yarn for fixing the main body of the valve on the outer surface of the eyeball, should be close, as far as possible, to the iris.

Instead, unfortunately, known drain valves have such a configuration as to involve a certain distance between these fixing holes and the iris, when it would instead be useful, for the reasons stated previously, i.e. to ensure more stable and robust attachment of the main body of the valve on the surface of the eye globe, for this distance to be smaller.

Among known drain valves intended for treatment of glaucoma and based on the principle of draining the aqueous humour contained in the anterior chamber so as to regulate the intraocular pressure, mention is made in particular of the so-called "Ahmed valve".

In any case this type of valve, despite the fact it has had and continues to have wide application in the treatment of glaucoma, is also not to be considered free from disadvantages and limits recalled previously, so as to require further improvement.

SUMMARY OF THE INVENTION

Therefore the primary object of the present invention is to make a drain valve implantable in an eye for the treatment of glaucoma which is a significant improvement with respect to current valves, and in particular is suitable for effectively remedying the various and numerous disadvantages, such as those previously listed and discussed, which afflict in fact the known drain valves currently applied in the medical field for the treatment of glaucoma and therefore considerably limit the performances and the efficacy thereof.

A further object of the present invention is also that of making a drain valve for the treatment of glaucoma which can be implanted easily on the eye of a patient and offers moreover greater and wider possibilities of action for the surgeon during the phase of implant of the valve, with respect to the valves known and applied, and for example gives the possibility to the surgeon of varying and adapting, taking account of the specific configuration of the eye globe, the distance between the main body of the valve fixed on the surface of the eye globe, under the conjunctiva, and the point wherein the drainage tube is implanted with its tip in order to penetrate the interior of the eye globe.

These objects are to be considered fully achieved by the implantable improved valve, for the treatment of glaucoma, having the features defined by the main independent claims 1, 11 and 16.

Particular and advantageous embodiments of the invention are moreover defined by the other dependent claims.

BRIEF DESCRIPTION OF THE DRAWINGS

These and other objects, features and advantages of the present invention will be made clearer and more evident by the following description of one of its preferred embodiments, given by way of a non-limiting example, with reference to the accompanying drawings, in which:

FIGS. 2A-2G are a series of images which illustrate a first improvement which characterises the drain valve of the invention of FIGS. 1A-1D and is intended to allow extraction or reinsertion of a distal drainage tube in an outer tube or sheath, in turn connected to a main body of the drain valve;

FIGS. 3A-3E are graphic three-dimensional images which illustrate a second improvement which characterises the drain valve of the invention of FIGS. 1A-1D, on the basis of which the distal tube, extractable from the outer tube or sheath of the drain valve, has a flattened shape in section;

FIGS. 4A-4E are graphic images which illustrate a third improvement which characterises the drain valve of the invention of FIGS. 1A-1D, and in particular show the zone of connection between a rigid end portion to be inserted in the anterior chamber of the eye, of the distal tube extractable from the sheath of the drain valve and the remaining flexible portion of this distal tube;

FIG. 8 is a sectioned plan view of a drain valve of the conventional type and complying with the prior art.

FIG. 9A is a schematic view of the zone of the eye which is intended to receive and in which the drain valve of the invention for the treatment of glaucoma is implanted; and FIG. 9B shows the area of the eye of FIG. 9A with the drain valve of the invention implanted.

DETAILED DESCRIPTION OF A PREFERRED EMBODIMENT OF THE INVENTION

Figure 1A:
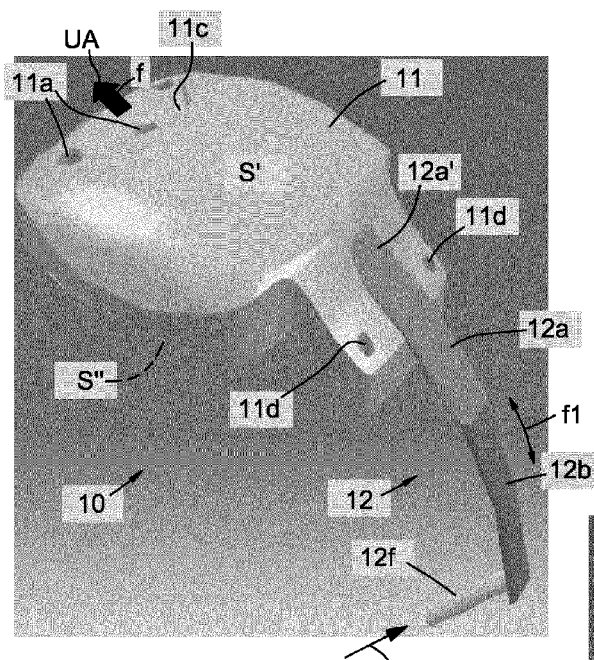
FIGS. 1A-1D are some graphic, schematic and partial images, which show in three-dimensional form, from various observation points, an improved drain valve, implantable in the eye of a patient, in accordance with the present invention, for the treatment of glaucoma.
Figure 1B:
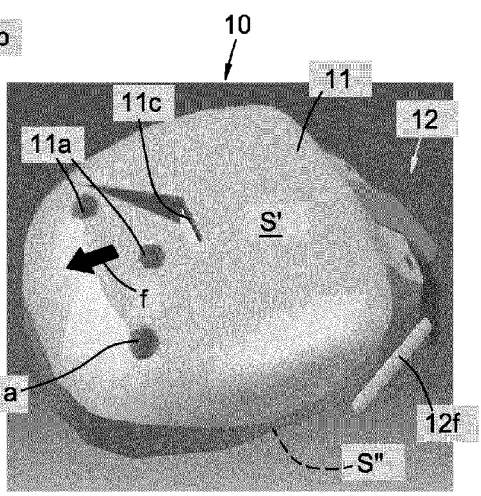
Figure 1C:
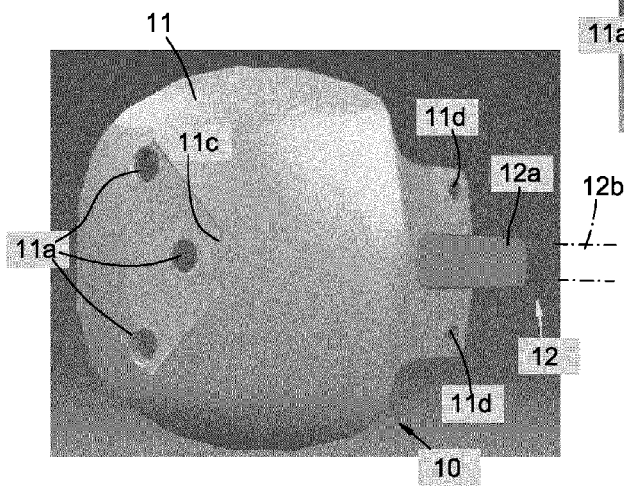
Figure 1D:
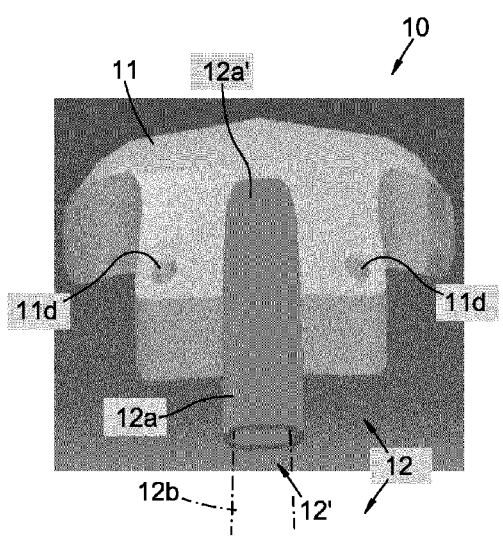

Referring to the drawings, a drain valve, in accordance with the present invention, implantable surgically in the eye O of a patient, in order to treat glaucoma, and in particular having the function of draining the aqueous humour UA contained in the anterior chamber CA of the eye globe GO, between cornea COR and iris IR, is denoted overall by 10.

For an easier and clearer understanding of the invention FIG. 9A shows schematically the zone of the eye O, with the parts previously mentioned, which is provided for receiving and in which is implanted the drain valve 10 of the invention.

In detail the drain valve 10 comprises:
a main body, denoted overall by 11; and
a drainage tube, denoted overall by 12 and connected at one end with the main body 11.

The main body 11 is designed to be fixed by the surgeon on the outer surface of the eye globe GO of the eye O, incising the sclera or scleral sac SC in an area under the conjunctiva CON which covers the same eye globe GO.

The drainage tube 12 in turn is provided to be positioned by the surgeon on the outer surface of the eye globe GO and to be implanted in the eye so as to penetrate, with its end or tip opposite the one connected with said main body 11, inside the eye globe GO and in particular in the respective anterior chamber CA, formed between the cornea COR and the iris IR of the eye O.

In this way the aqueous humour UA is drained from the anterior chamber CA towards the exterior of the eye globe GO, passing through the drainage tube 12 and the main body 11 of the drain valve 10, to then finally flow outside of the main body 11 in the area under the conjunctiva CON.

More particularly the drainage tube 12 can comprise:
a first portion, adjacent and connected at one end to the main body 11 of the drain valve 10, wherein this first portion is provided to be placed, during the surgical operation, along the outer surface of the eye globe GO, and
a second portion which is grafted at an angle of approximately 45° on the end, opposite the one connected to the main body 11, of the first portion of the drainage tube 12, wherein this second portion is provided in order to be implanted so as to perforate the outer surface of the eye globe GO and therefore penetrate its interior.

The first portion of the drainage tube 12, adjacent to the main body 11, extends inside the main body 11 to connect to a membrane valve device, denoted in general by 13, housed inside the same main body 11.

For the sake of clarity this membrane valve device 13 will be described in brief, referring to FIGS. 2A-2C.

More particularly the membrane device 13 comprises an elastic membrane 13a, constituted by a sheet of elastic material folded in two, wherein this elastic membrane 13a is placed between two small plates 13b and 13c housed in an outer shell of the main body 11 and reciprocally centred by means of a series of reference pegs or pins 13d.

The sheet folded in two of the elastic membrane 13a forms in turn an inner chamber which is connected and is in communication, in the zone of folding of the sheet, with the drainage tube 12, so as to receive the aqueous humour UA coming and drained from the anterior chamber CA.

In this way the elastic membrane 13a, housed inside the main body 11, receives and is subject also to the pressure of the aqueous humour UA coming from the anterior chamber CA, so that it reacts to this pressure by deforming, between the two small plates 13b and 13c, so as to open or close a crack formed by the folded sheet, in the zone opposite to that of the folding, and therefore regulate the flow, i.e. the drainage, as indicated by an arrow f in FIG. 1A of the aqueous humour UA from the anterior chamber CA outside of the main body 11 of the drain valve 10.

It is pointed out, as shown in the drawings, that the folded membrane 13a is completely smooth and therefore does not have, like instead the membrane of conventional drain valves, reference holes suitable for co-operating with corresponding small reference pegs or pins in order to position the same folded membrane 13a with respect to the small plates 13b and 13c between which it is housed.

Therefore, by means of this membrane valve device 13, the drain valve 10, once implanted by the surgeon on the eye of the patient, is able to diminish, thanks to the action of drainage of the aqueous humour from the inside towards the outside of the eye globe, the intraocular pressure which constitutes one of the negative effects of glaucoma.

The drain valve 10 of the invention is characterised by a series of significant improvements, which will be described here below.

First Improvement: Extractable Configuration of the Drainage Tube with End of Travel Stop According to this improvement, illustrated in FIGS. 2A-2G, the drainage tube 12 of the drain valve 10 of the invention has a telescopic or extractable configuration comprising a first outer tube, denoted by 12a and also referred to as outer sheath, connected at a respective end 12a' to the main body 11 of the valve 10 and to the respective membrane valve device 13, and a second inner tube, denoted by 12b and also referred to as distal tube, suitable for sliding in the outer tube 12a, as indicated by a double arrow fl, and therefore also for being variably extracted from the same first outer tube 12a.

In particular the second inner or distal tube 12b is constituted by a first portion 12b', sliding in the outer tube 12a, and by a second portion or intraocular tube, denoted by 12f and exhibiting in section a circular shape, which is grafted at an angle α of approximately 45°, i.e. an angle β of 135° according to how it is measured, as also shown in FIG. 2F, on one end, of the first portion 12b', opposite that which slides in the outer tube 12a.

The intraocular tube 12f in turn constitutes the tip portion, of the inner or distal tube 12b, which is implanted by the surgeon in order to penetrate the anterior chamber CA and drain the aqueous humour.

Therefore this extractable configuration of the drainage tube 12 has the advantage of allowing the surgeon to vary and adapt, during the operation to implant the valve, the distance between the respective main body 11 and the point wherein the drainage tube 12 is implanted on the surface of the eye globe GO to penetrate its interior.

Moreover the slanted configuration at 135° of the intraocular tube 12f, with respect to the portion 12b' of the distal tube 12b which slides in the sheath 12a, enormously facilitates the insertion and the penetration of the drainage tube 12 in the eyeball and in particular avoids the buckling of the distal tube 12b during the surgical operation to implant the valve.

A gasket 12c is associated with the end, of the inner tube 12b, sliding in the outer tube 12a, so as to ensure the sealing between the two outer 12a and inner 12b tubes of the drainage tube 12.

Moreover, as can be seen from the drawings, this gasket 12c also has a function of abutment or travel stop, so as to prevent the inner tube 12b from exiting and separating from the outer tube or outer sheath 12a, during the relative sliding between these two tubes 12a and 12b.

The outer tube 12a, adjacent to the main body 11, is connected at one end via an insert 12d with the membrane valve device 13 housed inside the main body 11 so as to convey into the membrane valve device 13 the aqueous humour UA drained by the drainage tube 12.

FIG. 2F shows schematically the configuration assumed by the drainage tube 12 in its smallest elongation, with the inner tube 12b completely withdrawn and retracted in the outer tube 12a.

FIG. 2G shows instead schematically the configuration which is assumed by the drainage tube 12, when it has its maximum elongation, in which the inner tube 12b abuts at one end, with the respective gasket 12c, against a ridge or abutment 12a", in turn formed by a narrowing at one end of the outer tube or outer sheath 12a.

Therefore, in the telescopic configuration of the drainage tube 12, the gasket 12c, associated with the inner tube 12b, allows advantageously a decrease in the friction forces between the outer surface of the same tube 12b and the inner one of the outer tube 12a, and also prevents the inner tube 12b from exiting and uncoupling from the outer one 12a.

During the operation for implanting the drain valve 10 of the invention, the surgeon, should he or she have the need, after having implanted the main body 11 of the valve 11, to elongate or adapt the length of the drainage tube 12, has only to pull and extract with pliers the second inner tube 12b, or to slide in the direction required the second tube 12b in the first tube 12a.

Then the surgeon, once the correct extraction length of the second inner tube 12b has been established, can insert and implant in the eye of the patient the tip of the portion, projecting from the outer tube 12a, of the same inner tube 12b, so that it penetrates the interior of the anterior chamber CA.

More particularly in this phase, as will be described here below, the surgeon, after having adapted the length of the drainage tube 12, inserts and implants in the eye of the patient the intraocular tube 12f, which corresponds to the tip portion of the second inner tube 12b and is orientated at an angle β of approximately 45°, as shown in FIG. 2F, with respect to the remaining portion 12b' of the same second tube 12b.

It is therefore clear that this first improvement defining a telescopic and extractable configuration of the drainage tube 12 is associated with major and tangible advantages during the performance of the surgical operation to implant the drain valve 10, such as for example:

- a series of easy and convenient operations for fixing and implanting the drainage tube;
- total lack of risk that the drainage tube can break due to excessive traction to which it could be subjected during the operation;
- easy positioning of the second inner tube, with the possibility of reinserting it, should it have been extracted excessively, in the first outer tube;
- low friction of sliding between the outer tube and the inner one and therefore the impossibility of adherence between these two tubes.

Second Improvement: Drainage Tube with Reduced Radial Dimension

According to this second improvement, illustrated in FIGS. 3A-3F, the drainage tube 12 of the drain valve 10 of the invention has in section, instead of a circular shape as in the valves of the prior art, a flattened or flat shape denoted by 12', suitable for decreasing, at the same sectional area available for the drainage flow of the aqueous humour UA, the dimension IR in the radial direction of the drainage tube 12 with respect to the surface of the eye globe GO.

For example this flattened shape in section can be made with an elliptical section shape, assumed both by the first outer tube 12a, directly connected to the main body 11 of the drain valve 10, and by the inner tube 12b, sliding in the tube 12a, or by only one of them.

In particular FIGS. 3A-3E show from several observation points and with different enlargements this second improvement, in the form wherein both the outer tube 12a and the inner tube 12b, sliding in the latter, exhibit a flattened shape in section. It is clear in any case that any shape in section suitable for decreasing, with the same sectional area available for the drainage flow of the aqueous humour UA the dimension IR in radial direction of the drainage tube 12 with respect to the surface of the eye globe GO is to be considered within this second improvement, so that this second improvement can be the subject of variants without departing from the scope of the invention.

More particularly the flattened shape in section 12' of the drainage tube 12 can be formed also when the drainage tube 12 does not have the telescopic and extractable structure, described previously, corresponding to the first improvement, i.e. when the drainage tube 12 is formed by a single tube without reciprocally sliding parts.

During the operation for implanting the drain valve 10, the drainage tube 12, exhibiting in section such a flattened configuration 12', is rested by the surgeon on the outer surface S of the eyeball GO, in such a way that the flat part of the drainage tube 12 is that which effectively comes into contact with the ocular surface.

It is therefore clear that this second improvement defining a flat or flattened shape of the drainage tube 12 is associated with major and tangible advantages both during the performance of the surgical operation to implant the drain valve 10 and subsequently in the effective use of the drain valve of the valve 10, once implanted, in the patient suffering from glaucoma, such as for example:
- a reduced dimension in radial direction with respect to the eye globe and therefore a low impact on the conjunctiva which covers the same eye globe,
- improved adherence of the drainage tube to the outer surface of the eyeball,
- adaptability of the drainage tube 12 to the curving of the eye globe GO.

Moreover this second improvement, thanks to the flat shape with reduced radial dimension of the drainage tube 12, effectively remedies the problem and the discomfort for the patient which the drainage tube, with circular section, creates in conventional drain valves, this section being circular due to its radial dimension hindering the movement of the eyelids PAL.

Third Improvement: Connection without Encumbrance Between the Tip Intraocular Tube and the Remaining Part of the Extractable Drainage Tube and Rigid Structure of the Intraocular Tube This third improvement, illustrated in FIGS. 4A-4E, relates to the zone of the intraocular tube 12f and in particular the zone of connection and of grafting, orientated at an angle of 45° or 135° as described previously, between the portion 12b', of the inner tube 12b, which is suitable for sliding in the outer tube 12a of the drainage tube 12 and exhibits in section the flattened shape 12' corresponding to the second improvement described previously, and the intraocular tube 12f, exhibiting a circular section, which is in turn provided in order to be implanted by the surgeon so as to penetrate with its tip 12f', having a tapered and sharp shape, inside the anterior chamber CA in order to drain the aqueous humour UA.

The present third embodiment is characterised, as clearly shown in FIGS. 4A and 4B, in that the connection between the portion or intraocular tube 12f and the other remaining portion 12b' of the inner tube 12b, sliding, is made by forming, on the surface of this other portion 12b', a blind hole 12e having a diameter exactly corresponding to that of the intraocular cylindrical tube 12f; inserting in the hole 12e the end, opposite the tip 12f', of the intraocular tube 12f; and creating a seal or a coupling, in the zone of this hole 12e, between the intraocular tube 12f, and the remaining portion 12b' of the inner tube 12b.

Moreover, to complete this connection, the end 12b" of the portion 12b' of the tube 12b, sliding, opposite the one placed towards the main body 11 of the valve 10, is closed and sealed with a sealing substance, for example by means of liquid silicone.

Therefore this third improvement allows advantageously a connection to be obtained between the intraocular tube 12f, of circular section, and the remaining part of the sliding inner tube 12b, in turn exhibiting in section the flat shape 12', with the intraocular tube 12f extended at an angle of approximately 135° with respect to this remaining part of the tube 12b, having a reduced radial and transverse dimension and in particular such as not to involve and not to have any additional encumbrance with respect to the shape of the same intraocular tube 12f and of the remaining part 12b' of the tube 12b in this connection zone.

Consequently, advantageously, also this third improvement remedies the disadvantage, which can be found in the known drain valves, of the encumbrance which is usually present in the zone of connection between the intraocular tube and the remaining part of the drainage tube, so that this third improvement eliminates the discomfort which such an encumbrance can cause the patient due to the obstacle which it creates to the movement of the eyelids.

Again this third improvement can easily be realised by exploiting the special flat and flattened shape in section of the portion 12b', sliding, of the inner tube 12b, whereon the intraocular tube 12f is grafted.

Moreover, advantageously, within the sphere of this third and of the other improvements described here which involve the drain valve 10, the intraocular tube 12f has a rigidity greater than that of the remaining portion 12b', instead flexible, of the inner or distal tube 12b, so as to facilitate the insertion by the surgeon of the intraocular tube 12f in the anterior chamber CA.

As shown in FIGS. 4D and 4E this third improvement also includes one or more incisions or cuts, denoted by 12g, which are formed along the outer cylindrical surface of the intraocular tube 12f and have the function of preventing the outflow of the same intraocular tube 12f, once implanted, from the eye.

FIGS. 4D and 4F also highlight the flattened shape, cut with a slant of approximately 45° with respect to the axis of the intraocular tube 12f, of the tip end 12f', of the latter, intended to perforate the eye globe.

Fourth Improvement: Compartments for Retaining the Aqueous Humour Along the Lower Surface of the Main Body of the Drain Valve in Contact with the Eye Globe This fourth improvement is aimed at improving and encouraging substantially the circulation of the aqueous humour, and consequently also the lubrication by the latter, in the area of resting and contact of the lower or soffit surface of the main body 11 of the drain valve 10 with the eye globe, so as to increase the adherence between these two parts and avoid the onset of infections.

In detail this fourth improvement comprises, as shown in FIGS. 5A-5F in some respective embodiments, a series of through holes, denoted by 11a, in particular three, which extend and are formed through the main body 11 of the drain valve 10, and which therefore have the function of placing in communication the surface of the eye globe, whereon the lower or soffit surface S" rests of the main body 11 of the drain valve 10 when it is implanted, and the upper or extrados surface S' of the same main body 11, opposite the lower one S", soffit, in contact with the eye globe GO.

Therefore these through holes 11a allow an effective circulation of the aqueous humour from the upper or extrados surface S' of the main body 11, which is the area where the aqueous humour drained by the valve and coming from inside the eye globe is poured, to lubricate the area of resting and contact of the main body 11 with the eye globe.

Moreover, in addition to these through holes 11a, this fourth improvement comprises, in order to improve further the lubrication of the area of contact between the main body 11 and the eye globe GO and therefore the adherence between these two parts, a series of compartments or recesses or bags, also referred to as retaining bags, denoted by 11b, which are formed along the lower or soffit surface S" of the main body 11 of the drain valve 10, which is placed in contact with the surface S of the eye globe GO, wherein each of these bags or compartments 11b is associated and formed at the base of a respective through hole 11a which extends through the main body 11 of the drain valve 10 of the invention.

Therefore these bags or compartments 11b, formed at the base of the through holes 11a, are suitable both for receiving a larger quantity of aqueous humour UA and for retaining it longer in time before it flows back, so as to facilitate and improve considerably the lubrication of the eye globe in the zone of the drain valve, after it has been implanted, and in particular lubricate a larger surface of the eye globe, with respect to known and commercially available valves which do not comprise these compartments, at the base of every through hole.

In summary this fourth improvement of the drain valve 10 of the invention, including both the through holes 11a and the retaining bags 11b formed at the base of each of these holes 11a, allows a considerably improved lubrication of the zone of the eye, including the eye globe, in which the valve 10 is implanted, so as to reduce considerably the risk of infections in this zone with respect to the known and currently used valves.

These retaining compartments or bags 11b, formed at the base of the through holes 11a, can take on various shapes and configurations and extend in various ways along the soffit surface S" of the valve body 11, always remaining within the scope of this fourth improvement.

Figure 5A:
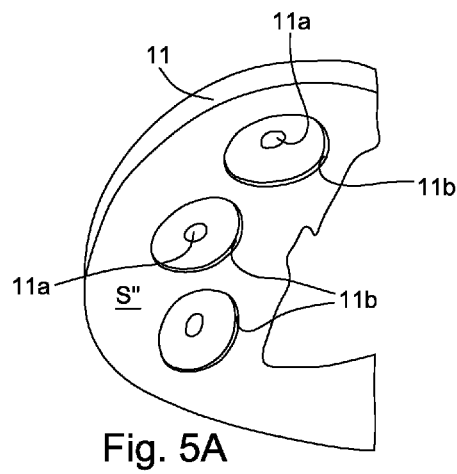
FIGS. 5A-5F are schematic perspective views and graphic three-dimensional images which illustrate a fourth improvement which characterises the drain valve of the invention of FIGS. 1A-1D, wherein this fourth improvement comprises a series of bags for retaining the aqueous humour formed on the soffit surface of the main body of the drain valve.
Figure 5B:
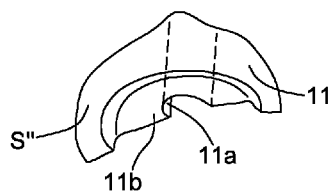
Figure 5C:
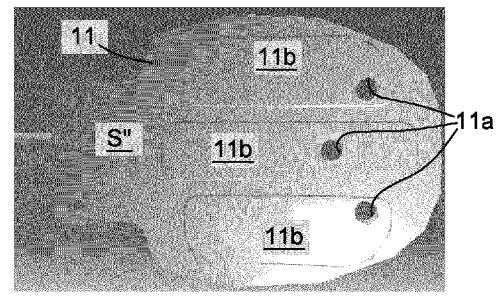
Figure 5D:
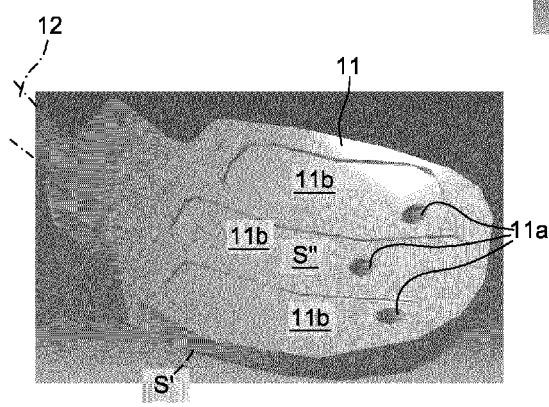
Figure 5E:
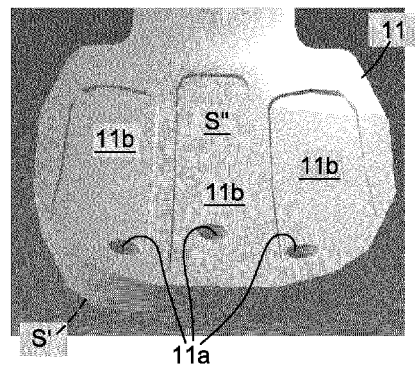
Figure 5F:
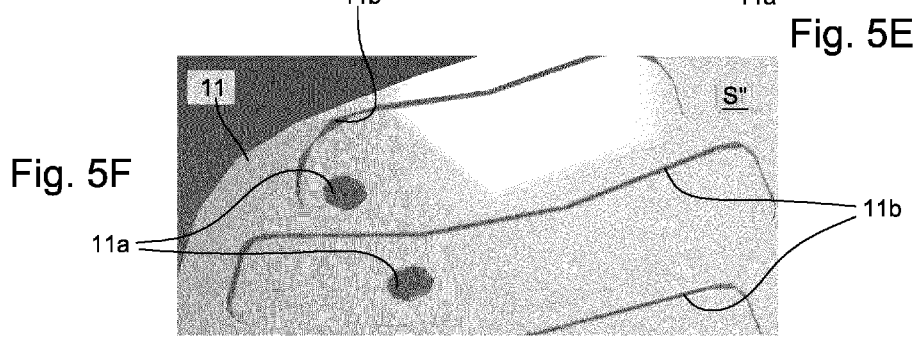

For example these compartments 11b can take on a substantially circular configuration, at the base of each through hole 11a, as shown in FIGS. 5A and 5B, or they can take on an elongated configuration in the longitudinal direction of the valve body 11, as shown in FIGS. 5C-5F.

Figure 6A:
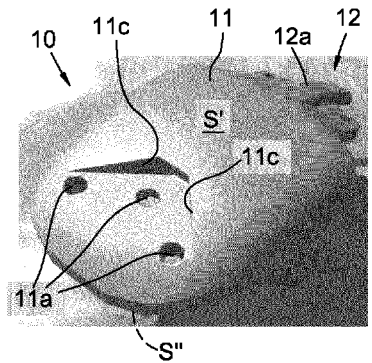
FIGS. 6A-6C are graphic three-dimensional images which illustrate a fifth improvement which characterises the drain valve of the invention of FIGS. 1A-1D.
Figure 6B:
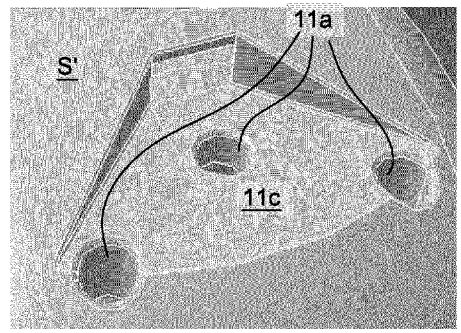
Figure 6C:
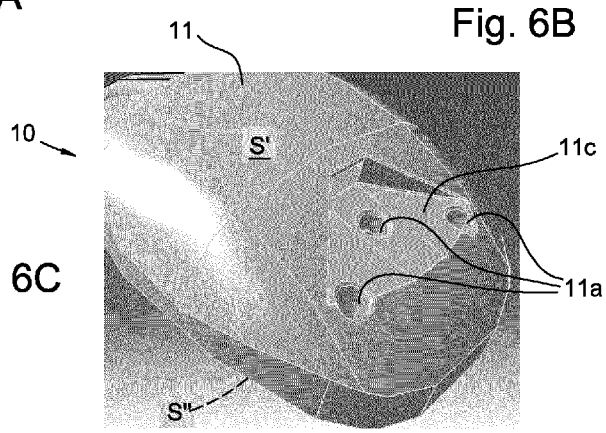

Fifth Improvement: Opening of Conveying with Fan Configuration of the Aqueous Humour in Place of the Ribs Present in Conventional Drain Valves According to this fifth improvement, illustrated in FIGS. 6A-6C, the upper or extrados face or surface S' of the main body 11 of the valve 10, opposite the lower or soffit surface S" of the main body 11, provided to be in contact and rest on the outer surface S of the eye globe GO, has an opening, denoted by 11c, defined by a divergent recess with fan configuration.

This opening 11c, with fan shape, is suitable both for facilitating the flow and the evacuation of the aqueous humour (UA) from the valve device 12, housed inside the main body 11 towards the upper or extrados surface S', of the main body 11, and to channel the aqueous humour UA, through the through holes 11a, towards the soffit S" of the main body 11 in contact with the surface S of the eye globe GO, so as to facilitate and improve the lubrication of the eyeball and of the other parts of the eye in the area adjacent to the drain valve 10.

In particular this opening 11c, with fan configuration, replaces advantageously the ribs present in known valves, so that the extrados S' of the main body 11 does not have any protuberance but a substantially smooth and even surface and is moreover, as previously mentioned, such as to improve the lubrication of the zone or the extrados S' of the same main body 11.

Therefore, advantageously, this fifth improvement, replacing the ribs with recesses, eliminates the disadvantage and the problem of the discomfort of the patient which these ribs create in conventional drain valves, these ribs being, due to their projection, an obstacle to the movement of the eyelids.

Sixth Improvement: Modified Arrangement of the Holes for the Insertion of the Yarn for Fixing of the Valve to the Eye Globe According to this sixth improvement, illustrated in FIGS. 7A and 7B, the drain valve 10 of the invention and in particular the respective main body 11 are characterised by a configuration, modified with respect to that of conventional drain valves, which allows the surgeon, in the operation for implanting the drain valve, to arrange the holes, for the insertion of the yarn for fixing the drain valve 10 to the surface S of the eye globe GO, in an adjacent position or closer to the iris of the eye, with respect to what is allowed by conventional drain valves.

In detail this new configuration of the drain valve 10, which is in fact made by elongating the relative main body 11 with respect to that of conventional valves, is such that the fixing holes, denoted by 11d, for the passage of the suture yarn of the drain valve 10 on the surface S of the eye globe, can be advantageously positioned by the surgeon at a distance closer by about 4 mm to the iris, with respect to conventional drain valves.

Figure 7A:
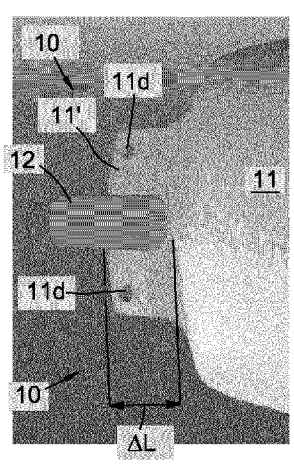
FIGS. 7A-7C are graphic images which illustrate, compared with the prior art, a sixth improvement which characterises the drain valve of the invention of FIGS. 1A-1D.

FIG. 7A shows this new configuration of the drain valve 10, which as anticipated previously is characterised in that the respective containing body 11 comprises an additional portion 11', of length ΔL, with respect to conventional drain valves, in which this additional portion 11' has the fixing holes 11d for the passage of the suture yarn, so as to allow, in the surgical operation, an adjacent arrangement thereof with respect to the iris of the eye.

Figure 7B:
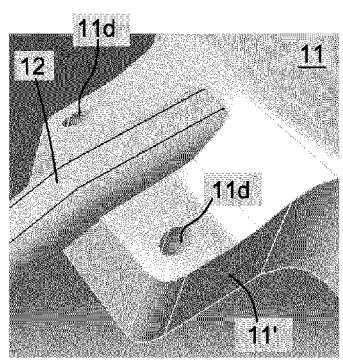

For greater clarity this additional portion 11' is shown in perspective form in FIG. 7B.

Figure 7C:
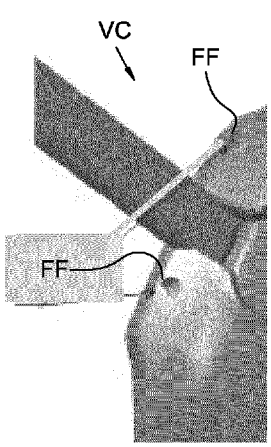

FIG. 7C in turn shows a conventional drain valve VC with the respective fixing holes, denoted by FF, which does not allow the aforesaid adjacent arrangement.

This sixth improvement is associated with multiple advantages and in particular facilitates the performance of the operation by the surgeon and also allows an optimal and improved anchorage of the drain valve to the surface of the eyeball.

Moreover a further improvement, for reasons of brevity not shown in the drawings, also provides for the end of the main body 11 of the drain valve 10 to be reinforced, i.e. exhibit a greater thickness, so as to facilitate, during the surgical operation, the insertion of the drain valve in the scleral sac or sclera.

In the surgical operation the surgeon fixes and implants the main body 11 of the valve 10 in the sclera or scleral sac SC and thanks to the extractable configuration of the drainage tube 12 slides as required the respective inner tube 12*b*, as indicated by a double arrow fl, so as to adapt the length of the drainage tube 12 to the configuration of the eye globe GO and at the point in which the surgeon wants to implant the drainage tube 12 to penetrate with its tip the anterior chamber CA.

For the sake of clarity, FIG. 9B shows the drain valve 10 of the invention, once it has been implanted by the surgeon in the eye O, in order to treat the glaucoma from which the patient is suffering.

It is therefore clear that, given numerous and relevant improvements introduced, the drain valve 10 of the present invention achieves in full all the objects which it had set.

It is likewise clear that the features, which define the various improvements, previously described, which characterise and distinguish the drain valve 10, can be combined in various ways one with the other, still remaining within the sphere and scope of the present invention.

In other words the features as previously described and illustrated with specific reference to a certain improvement can be advantageously combined with the features described in relation to another improvement or improvements, in other words be part and be applied in the context of other embodiments and other improvements, of the drain valve 10 of the invention, which have not been described here for reasons of brevity.

The invention claimed is:

1. Drain valve for the treatment of glaucoma, surgically implantable in an eye of a patient, comprising:
    a main body which accommodates a membrane valve device, and
    a drainage tube connected at one end with said main body and the respective membrane valve device,
    wherein said main body is designed to be implanted by a surgeon on an outer surface of the eye globe, in an area under the conjunctiva,
    wherein said drainage tube is suitable to be positioned by the surgeon on the outer surface of the eye globe and to be implanted in the eye so as to penetrate, with its end opposite to that adjacent and connected with said main body, inside the anterior chamber of the eye globe, in order to drain and feed from the anterior chamber to the membrane valve device the aqueous humor, and
    wherein said membrane valve device, accommodated in said main body, is suitable for controlling the drainage, towards the outside, of the aqueous humor contained in said anterior chamber and fed to the drainage tube;
    said drain valve being characterized in that said drainage tube has a telescopic configuration comprising a first outer tube, connected at one end to the main body and the membrane valve device of the valve, and a second inner tube suitable for sliding and thereby to be extracted from said outer tube, so as to allow the surgeon to vary and adapt, during the surgery to implant the drain valve, the length of the drainage tube depending on the distance between the main body of the drain valve and the point where the drainage tube is to be implanted on the surface of the eye globe to penetrate inside the anterior chamber,
    in that said second inner tube has a tip portion consisting of an intraocular tube provided to be implanted in the eye so as to penetrate inside the anterior chamber of the eye globe,
    in that said intraocular tube is grafted at an angle of 135° on a remaining part, sliding in said first outer tube, of the second inner tube, and has a rigidity greater than that of the remaining part of the inner tube;
    in that said drainage tube comprises a gasket integral with said inner tube and interposed between the latter and said outer tube in order to ensure the sealing of the drainage tube against the outflow of aqueous humor,
    in that, in the relative sliding of said inner tube with respect to said outer tube, said gasket, integral with said inner tube, is suitable for abutting against a ridge or a narrowing formed at one end of the outer tube in order to limit the sliding and the stroke of said second inner tube with respect to said first outer tube; and
    in that the main body of said drain valve has a series of through holes having the function of placing in communication an intrados of the main body, and thereby the outer surface of the eye globe on which the main body rests below, and the extrados of the same main body,
    wherein the intrados, of the main body of the valve, provided to rest and co-operate in contact with the outer surface of the eye globe, has at the base of and around each of said through holes, a retaining recess suitable for receiving and retaining the aqueous humor, so as to improve the lubrication of the area of contact between said main body and the eye globe and therefore the adherence between these two parts; and
    wherein an upper surface or extrados of the main body of the drain valve has an opening, defined by a divergent and fan-shaped recess, suitable for facilitating both the flow and the evacuation of the aqueous humor from the inside towards the outside of the main body and the channeling of the aqueous humor through said through holes towards the intrados of the main body in contact with the surface of the eye globe, so as to facilitate and improve the lubrication of the eye globe and of the other parts of the eye in the area around the drain valve.

2. Drain valve for the treatment of glaucoma, according to claim 1, wherein said drainage tube has a flattened or flat shape in section, so as to decrease, at the same sectional area available for the drainage flow of the aqueous humor, the dimension in the radial direction of the drainage tube with respect to the surface of the eye globe.

3. Drain valve for the treatment of glaucoma according to claim 2, wherein said flattened shape is defined by an elliptical shape in section of one or the other, or both, of the first outer tube and of the second inner tube of the drainage tube.

4. Drain valve for the treatment of glaucoma, according to claim 1, characterizes in that the grafted connection between said remaining part, sliding in said first outer tube, of the second inner tube, and said intraocular tube has a hole, which is formed on the surface of said remaining part of the second inner tube and in which one end of said intraocular tube is inserted, and a seal or gluing in the area of said hole between said remaining part and said intraocular tube, and in that the end of said remaining part of the second inner tube, adjacent to the area of the connection between said remaining part and the intraocular tube, is closed with a sealing substance.

5. Drain valve for the treatment of glaucoma, according to claim 1, characterized in that the drain valve has a configuration comprising an additional portion of the main body of the valve, exhibiting said fixing holes and being such as to elongate the length of the main body of the valve, whereby said configuration allows, during the surgery to implant the valve, an arrangement, closer to the iris, of the fixing holes for the insertion of the yarn for fixing the drain valve to the surface of the eye globe.

6. Drain valve for the treatment of glaucoma according to claim 1, wherein said drainage tube is connected at one end, via an insert, with the membrane of said membrane valve device housed inside the main body of the drain valve.

7. Drain valve for the treatment of glaucoma according to claim 1, wherein said membrane valve device, housed inside said main body, in turn comprises an elastic membrane suitable for receiving the pressure of the aqueous humor coming from the anterior chamber of the eye globe and for controlling in response the flow of the aqueous humor outwards of the drain valve, and wherein said membrane is devoid of holes for its positioning inside the respective membrane valve device.

8. Drain valve for the treatment of glaucoma according to claim 1, wherein the retaining recesses have a circular shape around the base of the respective through hole or a shape elongated along the longitudinal extension of the main body of the valve.

9. Drain valve for the treatment of glaucoma according to claim 1, wherein said intraocular tube includes one or more cuts which are formed along its outer surface and have the function of preventing the outflow of the same intraocular tube, once implanted, from the eye, and wherein the tip end of the intraocular tube, intended to perforate the eye globe, exhibits a flattened shape, cut with a slant of approximately 45° with respect to the axis of the intraocular tube.

* * * * *